US007706885B2

(12) United States Patent
Farone

(10) Patent No.: US 7,706,885 B2
(45) Date of Patent: Apr. 27, 2010

(54) TRANSCUTANEOUS ELECTRICAL NERVE STIMULATION AND METHOD OF USING SAME

(75) Inventor: William Farone, Irvine, CA (US)

(73) Assignee: Gradient Technologies, LLC, Memphis, TN (US)

( * ) Notice: Subject to any disclaimer, the term of this patent is extended or adjusted under 35 U.S.C. 154(b) by 345 days.

(21) Appl. No.: 11/678,528

(22) Filed: Feb. 23, 2007

(65) Prior Publication Data

US 2008/0207985 A1 Aug. 28, 2008

(51) Int. Cl.
*A61N 1/00* (2006.01)
(52) U.S. Cl. ........................................................ 607/46
(58) Field of Classification Search .............. 607/46–48
See application file for complete search history.

(56) References Cited

U.S. PATENT DOCUMENTS

| | | | |
|---|---|---|---|
| 4,431,002 A | 2/1984 | Maurer et al. | |
| 5,284,144 A | 2/1994 | Delannoy et al. | |
| 5,562,718 A * | 10/1996 | Palermo | 607/46 |
| 6,445,955 B1 * | 9/2002 | Michelson et al. | 607/46 |
| 6,675,045 B2 * | 1/2004 | Mass et al. | 607/32 |
| 6,741,889 B1 * | 5/2004 | Holcomb | 607/3 |
| 7,072,715 B1 | 7/2006 | Bradley | |
| 7,162,302 B2 | 1/2007 | Wang et al. | |

* cited by examiner

*Primary Examiner*—Mark W Bockelman
*Assistant Examiner*—Roland Dinga
(74) *Attorney, Agent, or Firm*—Bradley Arant Boult Cummings, LLP

(57) ABSTRACT

The present disclosure relates to an apparatus and associated methods to produce analgesia in a mammal by providing an electrical nerve stimulus utilizing a pulsed input of low level electrical current, wherein the level of current is measurable with the measurements utilized to at least adjust the strength of the current according to selected parameters. Additionally, the use of magnets to produce a magnetic field to further control chronic and acute pain. In exemplary implementations, the apparatus maintains continuous monitoring of the electrical characteristics of TENS at the site of input and output, and the electrical input can be modified during treatment to obtain desired electrical input. More particularly the disclosure relates to an electromagnetic apparatus incorporating pulsed direct current, two or more electrodes, and at least two dipole antennas wherein the dipole antenna circuits receive and analyze signal from the dipole antennas, using the information from signal analysis within the methods for producing analgesia in mammals. The strength of the current that the patient is receiving at the targeted site as the actual field is measured by the dipole antennas and adjustment is not dependent on subjective measurements to ascertain whether the proper amplitude, frequency and pulse duration are being applied.

27 Claims, 7 Drawing Sheets

Figure 17.14 A: Electrode positions for common pain conditions—anterior view. B: Electrode positions for common pain conditions—posterior view.

Figure 8. Example QMA Magnetic Field plot.
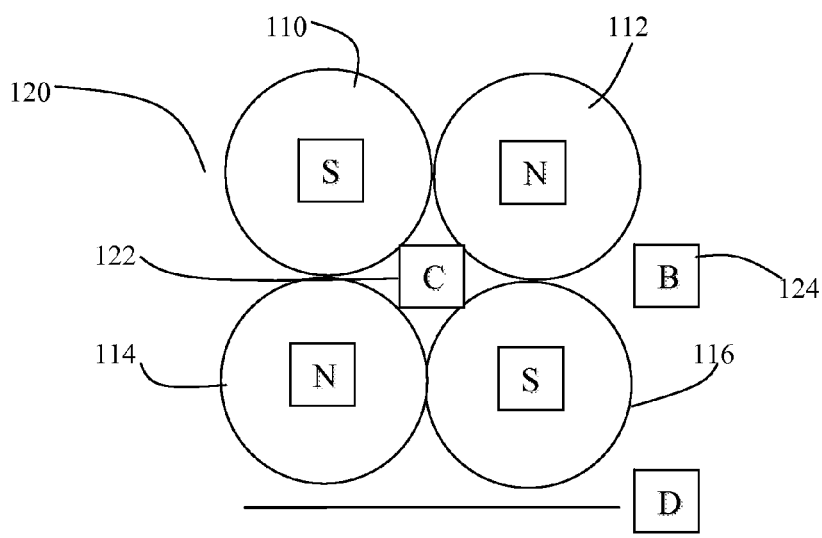
Figure 9. Plan layout of QMA showing North and South poles of magnets.

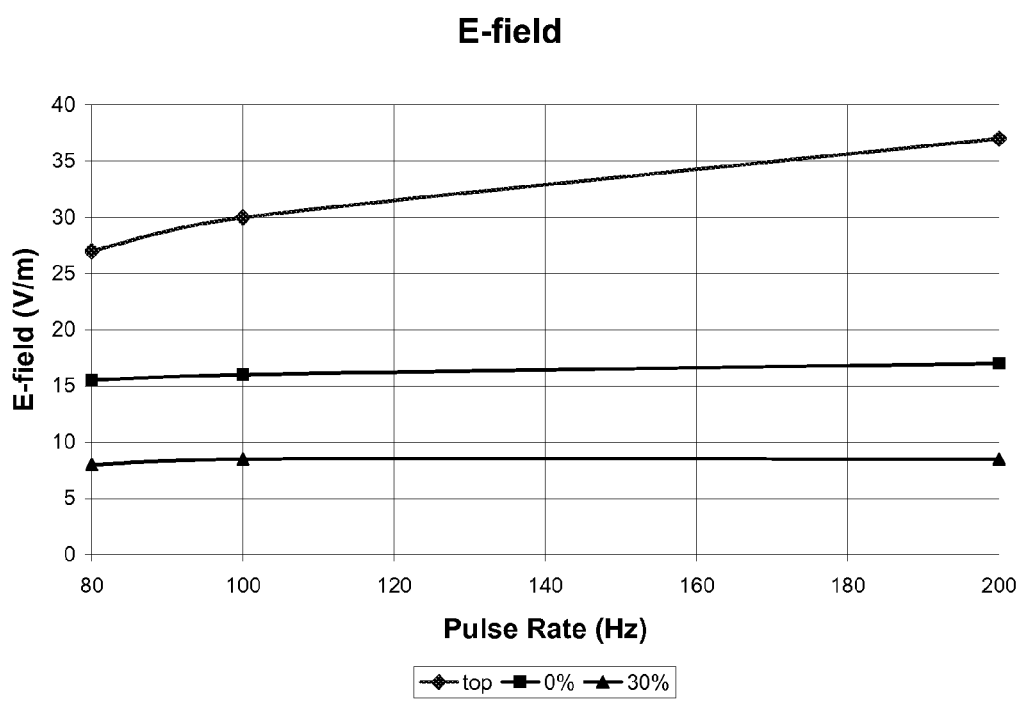
Figure 10. E-fields at Top and Bottom of Flesh

TRANSCUTANEOUS ELECTRICAL NERVE STIMULATION AND METHOD OF USING SAME

BACKGROUND

1. Field

The present disclosure relates to an apparatus and associated methods to produce analgesia in a mammal by providing an electrical nerve stimulus utilizing a pulsed input of low level electrical current, wherein the level of current is measurable with the measurements utilized to at least adjust the strength of the current according to selected parameters. Additionally, the use of magnets to produce a magnetic field to further control chronic and acute pain.

2. General Background

Electrotherapy and Pain

There are multiple pharmacologic approaches to the medical treatment of acute and chronic pain. Some of the pharmacologic treatments include acetaminophen, nonsteroidal anti-inflammatory drugs, glucosamine chondroitin, cyclooxygenase-2-selective inhibitors, topical analgesics, and opiate analgesics. Some of the nonpharmacologic options include physical therapy, such as aquatherapy, heat, and aerobic exercises, weight reduction for arthritic pain, bed rest, and osteopathic manipulative treatments.

In the 1960's the medical use of electricity was considered and various physiological rationale were proposed for its electroanalgesic effects. It was observed that chronic pain relief was obtained in some patients when high-frequency percutaneous electrical stimulation was used.

Transcutaneous Electrical Nerve Stimulation Mechanism and Muscle Contraction

Transcutaneous electrical nerve stimulation (TENS) controls pulsed currents delivered through the intact surface of the skin by conducting pads, referred to as electrodes. There are a variety of TENS-like devices available in the market. This proliferation of TENS-like devices has created literature which contains inconsistent nomenclature and ambiguous results in treatment. There are primarily three types of TENS: conventional TENS described herein, acupuncture-like TENS, and intense TENS.

The electrical characteristics of TENS are typically chosen to selectively activate different populations of nerve fibers. In post surgery/disease/injury related physical therapy TENS is used to contract muscles to maintain muscle tone when patients are unable to use the muscles normally. Large diameter nerve fibers (A$\beta$ and A$\alpha$) have low thresholds of activation to electrical stimuli when compared to the smaller diameter nerve fibers (A$\delta$ and C). The current amplitude needed to excite a nerve fiber declines as the pulse duration and pulse frequency increases. Therefore one would select low-intensity, high frequency currents with pulse durations between 10 and 1000 microseconds to activate the larger diameter fibers. Conversely increasing the pulse duration will lead to activation of the smaller nerve fibers at lower pulse amplitudes. Manufacturers have introduced features on TENS devices such as modulated amplitude, modulated frequency to assist in controlling muscle response.

TENS is also used to induce analgesia. TENS produces analgesia by a segmental mechanism where the activity generated in the A$\beta$ nerve fibers inhibit ongoing activity in the second-order nociceptive, i.e., pain related, neurons in the spinal cord's dorsal horn.

Transcutaneous Electrical Nerve Stimulation and Pain

Transcutaneous electrical nerve stimulation is a simple non-invasive technique that is used in health care settings by nurses, physiotherapists, and other health-care professionals. TENS is defined by the American Physical Therapy Association as the application of electrical stimulation to the skin for pain relief.

Nadler (2004) in a review of nonpharmacologic treatments indicated that TENS treatment caused about a 50% reduction in pain as opposed to a placebo response.

Maurer et al. (U.S. Pat. No. 4,431,002) and Holcomb (U.S. Pat. No. 6,741,889) indicated that pain relief could occur when electrical pulses were applied to the surface of the body or to electrodes which were implanted within the body. These TENS apparatuses provide electrical nerve stimulus where the stimulus pulses were modulated in both time and intensity in a prescribed manner.

TENS can activate different populations of nerve fibers. Low thresholds of activation to electrical stimuli have been found for the large diameter nerve fibers (A$\beta$ and A$\alpha$) when they are compared to nerve fibers, A$\delta$ and C (smaller diameter). As the pulse duration and pulse frequency increases, the amount of current amplitude which is needed to excite a nerve fiber decreases. To activate the larger diameter fibers such as A$\beta$ and A$\alpha$ typically one would select low-intensity, high frequency currents wherein the pulse durations are between 10 and 1000 microseconds. At lower pulse amplitudes the smaller diameter nerve fibers are activated with an increased pulse duration. Features such as modulated amplitude, modulated frequency, and duration have been introduced on TENS devices.

Conflicting reports have been published about the efficacy and the duration of a TENS application. Factors which contribute to these conflicting reports include (1) stimulus variables not controlled, (2) effect of different electrode placements, (3) dependent on patient's response, and (4) no means of measuring the electrical current applied to the locale undergoing treatment. It is difficult to predict the nature and the distribution of the currents when they pass across the surface of the skin due to the impedance of the tissue. Thus, at present the evidence for TENS effectiveness for chronic pain is inconclusive.

All publications, including patents, published patent applications, scientific or trade publications and the like, cited in this specification are hereby incorporated herein in their entirety.

SUMMARY

Increasing the Effectiveness of Transcutaneous Electrical Nerve Stimulation for Pain In exemplary implementations, the apparatus maintains continuous monitoring of the electrical characteristics of TENS at the site of input and output, and the electrical input can be modified during treatment to obtain desired electrical input. More particularly the disclosure relates to an electromagnetic apparatus incorporating pulsed direct current, two or more electrodes, and at least two dipole antennas wherein the dipole antenna circuits receive and analyze signal from the dipole antennas, using the information from signal analysis within the methods for producing analgesia in mammals. One avoids the problem of not knowing the strength of the current that the patient is receiving at the targeted site as the actual field is measured by the dipole antennas and adjustment is not dependent on subjective measurements to ascertain whether the proper amplitude, frequency and pulse duration are being applied.

In one implementation the signal from the dipole antenna is used to adjust the pulsed direct current output from the electrode by analyzing the signal delivered from the antenna. In a further aspect, the pulsed direct current is between about 1 volt to about 200 volts. In a further implementation the pulsed direct current is between about 20 volts to about 40 volts.

Another implementation the dipole antenna of the TENS apparatus are between about 1.5 inches to about 2.5 inches long and between about ¼ inch and about ¾ inch wide. In one implementation the dipole antenna materials are selected from conductor metals. In a further implementation the dipole antenna material is selected from the group consisting of copper, aluminum, and gold. In another implementation copper is the conductor material of the dipole antenna.

The apparatus produces analgesia in a mammal using the apparatus as described whereby there is continuous monitoring of the electrical characteristics of TENS at the site of input and output, and the electrical input can be modified during treatment to obtain the electrical input to produce the desired analgesia. In a further aspect, an electromagnetic apparatus incorporating pulsed direct current, two or more electrodes, and at least two dipole antennas wherein the dipole antenna circuits receive and analyze signal from the dipole antennas and this analyzed information is utilized to set the appropriate levels of pulsed direct current to produce the analgesia is disclosed.

In particular, analgesia in a mammal is produced by applying pulsed direct current to skin, analyzing electric field produced by the pulsed direct current, and then modifying strength of said pulsed direct current based on the measurements of the electric field. In one implementation the duration of the pulse is between about 10 microseconds to about 1000 microseconds. Another implementation the pulse duration of the direct current is about 50 microseconds to about 500 microseconds. In a further implementation the duration of the pulse is between about 100 microseconds to about 120 microseconds.

Further the frequency of the pulsed direct current is between about 1 pulse per second to about 250 pulses per second. In an additional implementation the frequency is between about 100 pulses per second to about 225 pulses per second. A further implementation the frequency of the pulsed direct current is between about 180 pulses per second to about 200 pulses per second.

In one implementation the pulsed waveform is selected from the group consisting of monophasic, symmetrical biphasic and asymmetrical biphasic waveforms. The waveforms are illustrated in FIG. 3. In a further implementation the pulsed waveform is monophasic waveform.

An additional implementation the pulsed current amplitude is adjustable between about one mA to about 50 mA into a 1 kilo Ohm load. In another implementation the pulsed current amplitude is between about 20 mA to about 40 mA. Further implementations comprise the pulsed pattern in a continuous or modulated wave shape, and in an additional implementation the pulsed pattern is a continuous wave shape.

Thus, one of ordinary skill in the art, using the methods and apparatus of the present disclosure, can avoid the problems associated with the methods for using existing TENS devices.

In another implementation, the apparatus involves a novel solution for producing analgesia in a mammal using the apparatus as described whereby there is continuous monitoring of the electrical characteristics of TENS using at least two dipole antennas wherein the dipole antenna circuits receive and analyze signal from the dipole antennas.

There is described a method of producing analgesia in a mammal applying pulsed direct current to skin of said mammal; analyzing electric field produced by said pulsed direct current; and modifying strength of said pulsed direct current based on measured said electric field using at least two dipole antennas wherein one antenna is placed for reference measurements and the second antenna is placed to measure all or partially the current field going to the mammal and the ratio of the antenna signals are used to adjust the settings.

In one implementation the dipole antennas are between about 1.5 inches to about 2.5 inches long and between about ¼ inch to about ¾ inch wide. The material of the dipole antenna is chosen from conductor metals. In a further implementation the conductor metal for the dipole antenna material is selected from the group consisting of copper, aluminum, and gold.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items The term 'skin' refers to the natural protective covering of a mammal's body. An equivalent definition refers to the membranous tissue forming the external covering or integument of a mammal and consisting in vertebrates of the epidermis and dermis. Stedman Medical Dictionary states: 'the 2-layered covering of the body consisting of an outer ectodermal epidermis that is more or less cornified and penetrated by the openings of sweat and sebaceous glands and an inner mesodermal dermis that is composed largely of connective tissue and is richly supplied with blood vessels and nerves'.

The term 'mammal' refers to any of various warm-blooded vertebrate animals of the class Mammalia, including humans.

The term 'conductor' refers to a substance or medium that conducts heat, light, sound, or an electric charge. The term also refers to a material or object that permits an electric current to flow easily.

The term 'TENS' refers to any stimulating device which delivers electrical currents across the intact surface of the skin.

The term "STENS" refers to a special TENS device of the present disclosure designed to provide transcutaneous electrical nerve stimulation to a mammal in a regulated or measured manner.

The term "pulse width" refers to the duration of a pulse from the time it is turned on to the time it is turned off.

The following abbreviations are used:
IC; Integrated Circuit
A/D; Analog to digital
LCD; Liquid crystal display
LED; Light emitting diode
QMA Quadrapolar magnetic array All publications, including patents, published patent applications, scientific or trade publications and the like, cited in this specification are hereby incorporated herein in their entirety.

DRAWINGS

The foregoing aspects and advantages of present disclosure will become more readily apparent and understood with reference to the following detailed description, when taken in conjunction with the accompanying drawings, wherein:

FIG. 8 illustrates the QMA Magnetic field plots.

FIG. 9 illustrates the layout of QMA showing North and South poles of magnets.

FIG. 10 illustrates the measured electric fields utilizing the disclosed apparatus and method.

The Figures are diagrammatic and are not drawn to scale. Corresponding parts generally bear the same reference numerals.

DETAILED DESCRIPTION

An apparatus generally for use in methods of relieving pain in mammals is disclosed.

Figure 1:
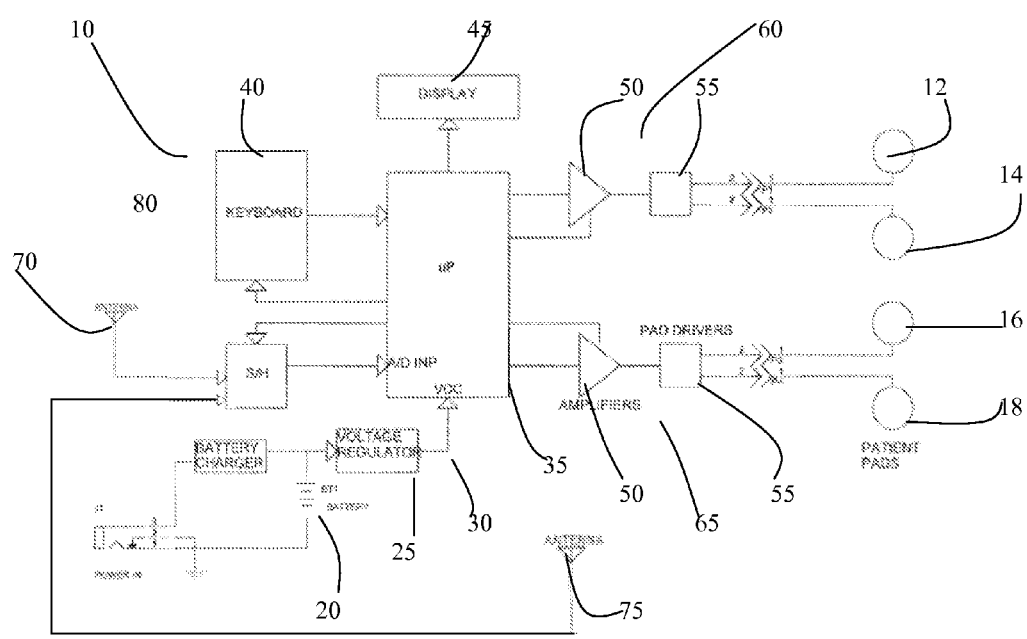
FIG. 1 illustrates a Block Diagram of a STENS unit

Referring now to FIG. 1 the block diagram illustrates the features of a Special TENS (STENS) device 10 designed to provide Transcutaneous Electrical Nerve Stimulation to mammal bodies. The device 10 does so by providing a high voltage pulse to conductive adhesive pads 12, 14, 16, 18, or patient pads, placed on the body.

Power for all operation and stimulation pulses is provided by the battery pack 20. The battery pack 20 may vary in size and in number of cells depending on battery life required and weight limits for a convenient product weight. The cells used are typical alkaline type found in numerous retail outlets. The system can also accept NiCd or NiMH rechargeable cells as well.

There is a voltage regulator 25 that takes the battery voltage and converts it to a regulated voltage 30 required by the microprocessor 35. As the battery pack 20 discharges and its output voltage decreases, the voltage regulator holds the regulated voltage to a constant voltage. In one implementation the regulator is a boost configuration as the battery voltage is always lower than voltage 30 required by the microprocessor 35.

The microprocessor 35 controls all functions of the STENS unit 10, interprets the keyboard 40 entries, places status information on the display 45, controls the amplifier 50 output voltage, and creates the pulses at the proper duration and repetition frequency to transmit the current to the patient therapy pads 12, 14, 16, 18. The microprocessor 35 has the ability to store the program code on a chip as well as having counters for keeping track of pulse duration, treatment time, and frequency. The microprocessor 35 has an on-board time base to run its internal logic and this is also used for timing external operations such as pulse width and treatment time. There are also a multitude of input and output ports through which the processor controls external functions and receives information. The processor has built in channels capable of interpreting analog values (A/D Inputs).

The keyboard 40 is a standard X, Y matrix of rows and columns where a key will connect a unique row to a unique column. This key is then recognized by the microprocessor 35 as it sequentially drives individual X rows and senses the voltage on the Y columns.

The display 45 can be of any variety commonly available. Vacuum fluorescent, LCD, LED, and plasma displays would provide equivalent displays. The purpose of the display unit 45 is to list operating parameters of the STENS unit 10. In the presently disclosed apparatus, an alpha numeric LCD module was used in the first implementation and a custom type icon based LCD is available for use in further implementations. The alphanumeric display offered great flexibility in displaying information, but had limitations in displaying simultaneous information. The alphanumeric display is cost effective and is widely available.

There are two channels 60, 65 for therapeutic output. These channels 60, 65 each have two wires between which a voltage potential is created. The amplitude, pulse width, pulse frequency, and time of application are all controlled by the microprocessor 35.

For amplitude control the microprocessor 35 communicates to a digital potentiometer associated with each channel amplifier 50. Since the amplitude of each channel 60, 65 is independent of the other channel, there are two amplifiers 50; i.e, the first channel 60 amplitude does not depend on the amplitude of the second channel 65. The amplifiers 50 boost the battery voltage to an intermediate voltage which is controlled, and sends a signal to the pad drivers 55. The pad drivers 55 amplify the voltage, which was previously boosted by the voltage regulator 25, by a fixed ratio and sends the voltage as a potential between the two pads 12, 14, 16, 18 associated with a particular channel 60, 65. Each channel 60, 65 is galvanically isolated from the other channel and also isolated from the primary circuit attached to the battery 20 and processor electronics.

To measure field effects created by the potential applied to the stimulation pads (patient pads), there are two antennas 70, 75 which detect the electric field. Because the antennas 70, 75 pick up fields created by all 60 Hertz electric appliances and wiring in the vicinity as well as random electrical noise, Signal Conditioning circuitry is provided which acts as a high pass filter, attenuating the 60 Hertz signal. This filter circuit eliminates all low frequency signals which are considered interference from extraneous 60 Hertz electric appliances and wiring in the local vicinity. When a pulse is detected, the antenna signal must be read shortly after it is detected. In one implementation this is done with a Sample and Hold circuit 80. This holds the peak of the detected output signal. These circuits are available integrated onto a single IC. In another implementation this function is preformed by using the built in A/D converter on the microprocessor 35. Basically, the processor is taking a picture at a specific moment in time, and this captures the amplitude of the wave form at that particular time. By capturing this information at the same time after the start of each output pulse, the peak amplitude is captured, and the need for a sample and hold circuit is eliminated. The information from this antenna measurement is one of the parameters which can be viewed by the user on the display. The information from the antenna measurement may also be used for adjusting therapy parameters thereby forming a closed loop feedback system wherein the therapy is adjusted to stay within the therapeutic window.

Figure 2:
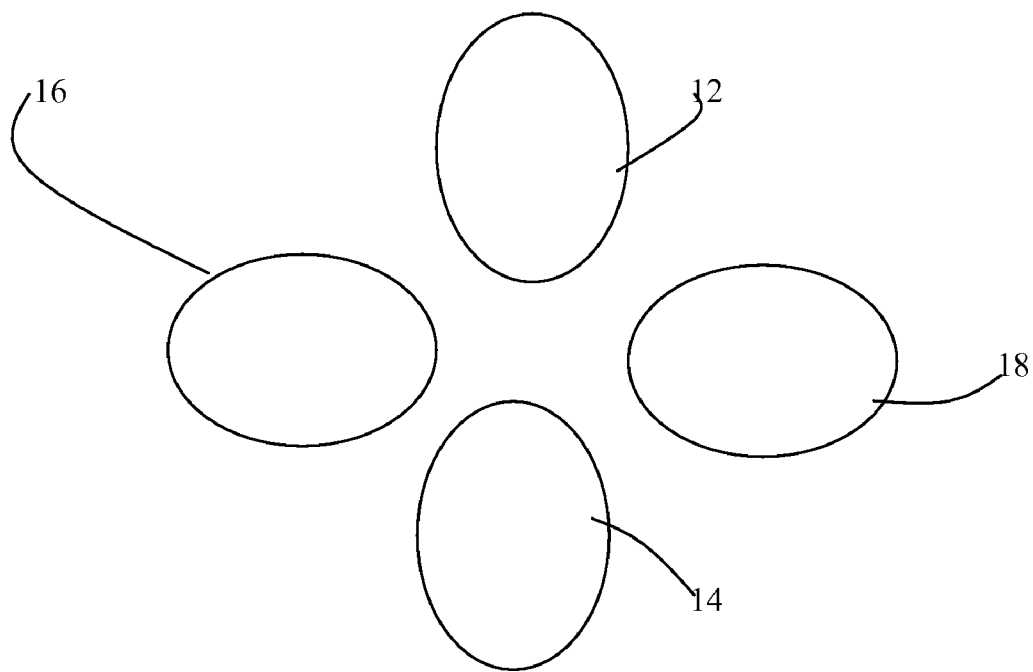
FIG. 2 illustrates an exemplary implementation showing one potential configuration of patient pads.
Figure 3:
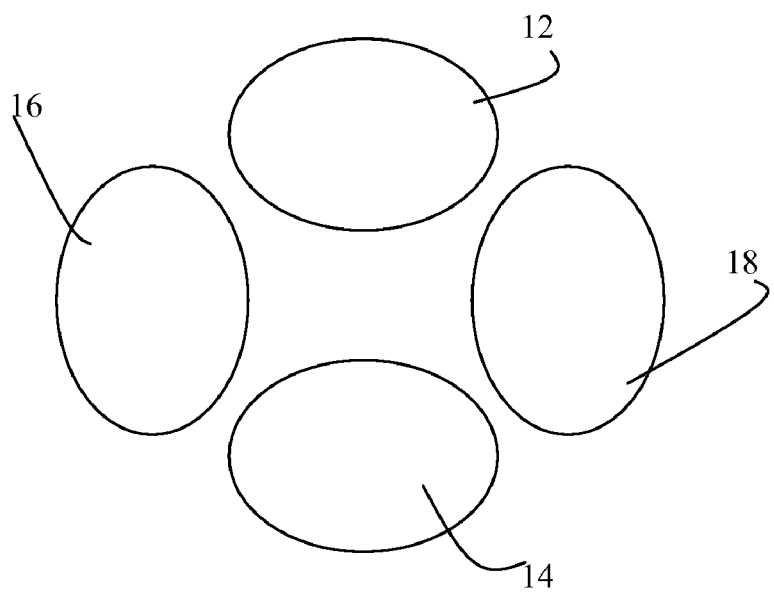
FIG. 3 illustrates another exemplary implementation showing an additional potential configuration of patient pads.

There are two antenna circuits, each tied to one of the output channels. One antenna 70 can be placed in the vicinity of the patient pads and the other antenna 75 on the opposite side of the area to be treated. Thus, as an example only, if two sets of patents pads 12, 14, 16, 18 were placed over the frontal area of the knee with an antenna 70 located adjacent to the pads and the second antenna 75 placed behind the knee, the difference in signal strength would indicate the intensity of the current at a desired point within the knee itself. FIGS. 2 and 3 show two different configuration of arrangement of patient pads 10, 12, 14, 16 on an individual for treatment. The configuration in FIG. 2 gives a sharper gradient at the pain point which is located between the pads (electrodes). In the configuration in FIG. 3 the current flow is spread out and will impact more neurons where the pain is diffuse. Either configuration of pads/electrodes 12, 14, 16, 18 can be read by the antenna system. The two antennas 70, 75 reference the signal and the field to be used is based on the difference between the two signals. With either configuration one would put one antenna 75 in the center of the pads 12, 14, 16, 18 and the other antenna can be referenced back to the first antenna 70 to obtain a relative reading for use in adjusting the field. There are normally four variables involved in adjusting the field, the voltage setting on the TENS unit 10, the current width, the current pulse rate and the actual position of the electrode (patient) pads 12, 14, 16, 18.

Figure 7:
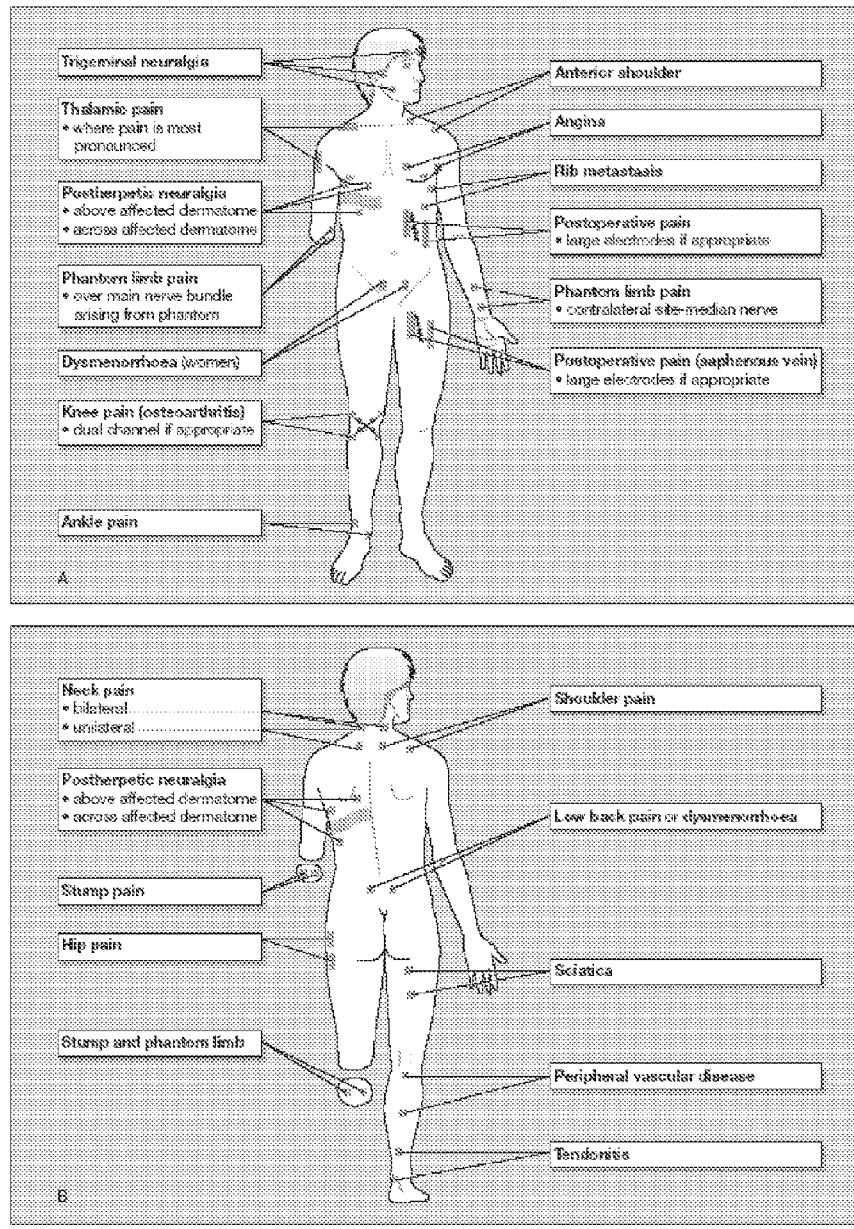
FIG. 7 illustrates the various locations for the placement of electrodes for pain relief utilizing the disclosed apparatus and method.

FIG. 7 illustrates additional sites 100 on a human where electrodes 12, 14, 16, 18 could be placed for the relief of pain as indicated. It is to be understood that the use of the apparatus and method is not limited to these sites and that the apparatus can be practiced at various other sites within the scope of the claims.

Figure 6:
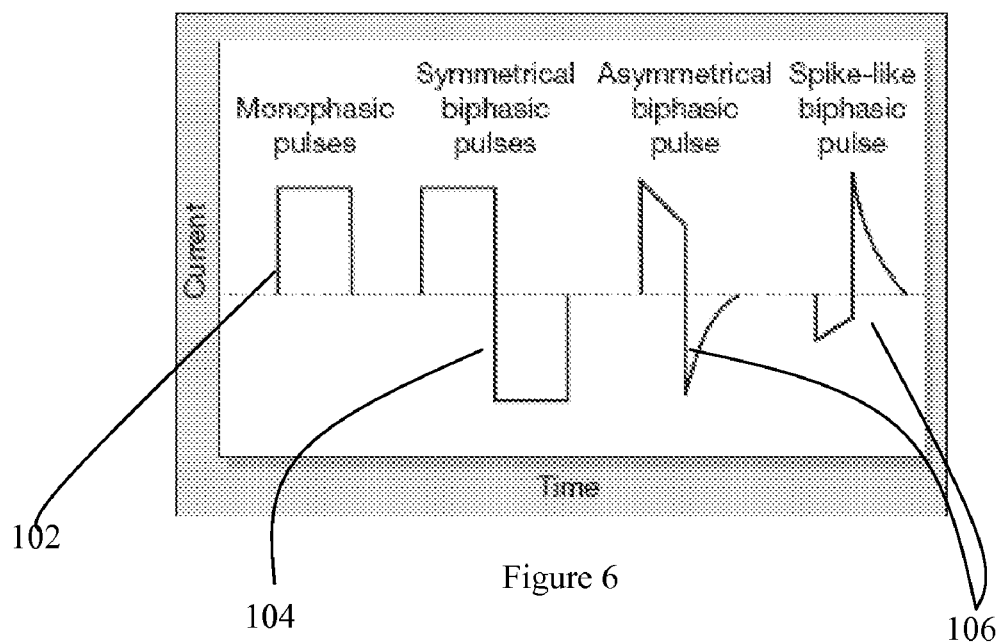
FIG. 6 illustrates the pulse waveforms in exemplary implementations of TENS.

The TENS unit 10 as described herein is a method for producing analgesia in mammals via a pulsed input of direct current as a low level at the surface of the skin. The pulsed waveform can be monophasic 102, symmetrical 104 or asymmetrical biphasic 106 as illustrated in FIG. 6. The pulsed amplitude is adjustable at 1 to 50 mA into a 1 kilo Ohm load. The pulse duration is 10 to 1000 microseconds and can be fixed or variable but typically is fixed. The frequency is adjustable over the range of 1 to 250 pulses per second which is continuous (for the duration of the pulse) or modulated either by frequency or amplitude. There is a channel 60, 65, per pair of electrodes.

The electrodes 12, 14, 16, 18 are used in pairs with the current passing from one electrode to the other. Each electrode pair has a plus and minus polarity.

The current is dependent on the resistance between the electrodes 12, 14, 16, 18. In the skin the pulse creates an electric wave (an electric field) that is emanated into space and into the mammal being treated. The electric wave field creates a current at the site of neuronal firing that can interfere with or block the transmission of pain signals. When the current at the site of application has too high an output, then there is muscle stimulation; i.e., cause the muscle to contract in response to the electric field.

When a TENS unit 10 is used for pain relief one provides a field of sufficient amplitude at the site of the pain to cause disruption of the pain signal. This value is highly variable from person to person as the electrical field is adsorbed by tissue and bones present at the site. The method of this present disclosure provides a means of assuring the delivery of the field to the desired site of action.

A magnetic field can also be used to reduce pain by deflecting the electrons that are "fired" during the neuron firing. This is described in U.S. Pat. Nos. 5,312,321, and 6,461,288. A magnetic field deflects the charge. In the case of pain communication, the charges are carried by cations of potassium, sodium and calcium that shuttle between receptors. The magnetic field keeps the cations from hitting the target receptor because the magnetic field moves the charge perpendicular to the field direction. The higher the field gradient the more the deflection.

Figure 4:
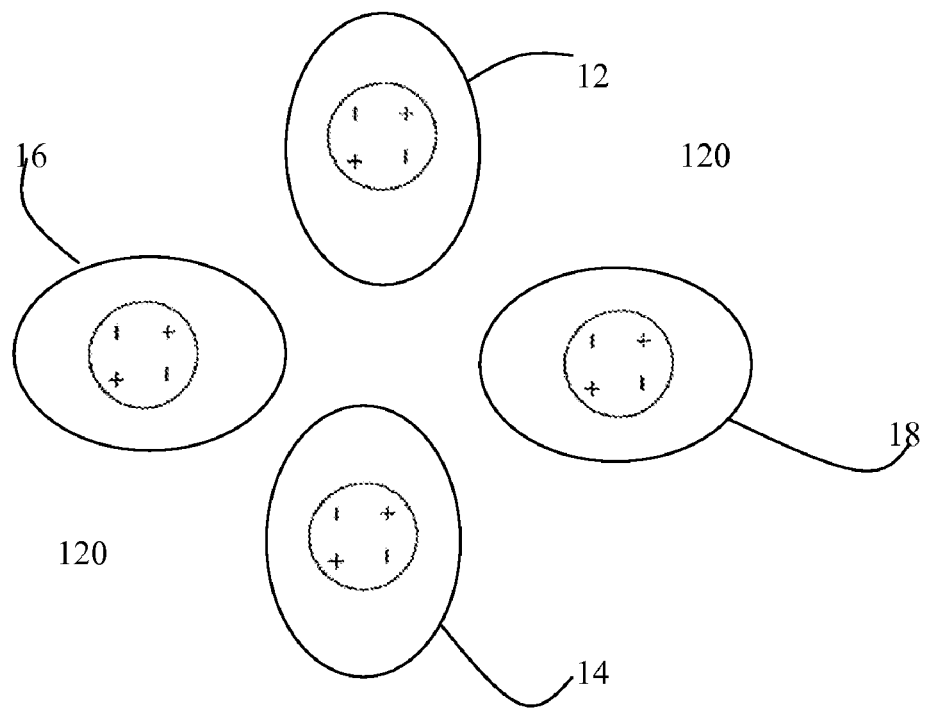
FIG. 4 illustrates an exemplary implementation showing one potential configuration of patient pads including a QMA located on each of the electrode pads.

As described in U.S. Pat. Nos. 6,205,356 and 6,741,889 and illustrated in FIG. 4, Holcomb combined the use of a specific arrangement of magnets 110, 112, 114, 116 (quadrapolar magnetic arrays—QMAs) over each electrode of a TENS unit 10 to provide increased pain relief.

Figure 5:
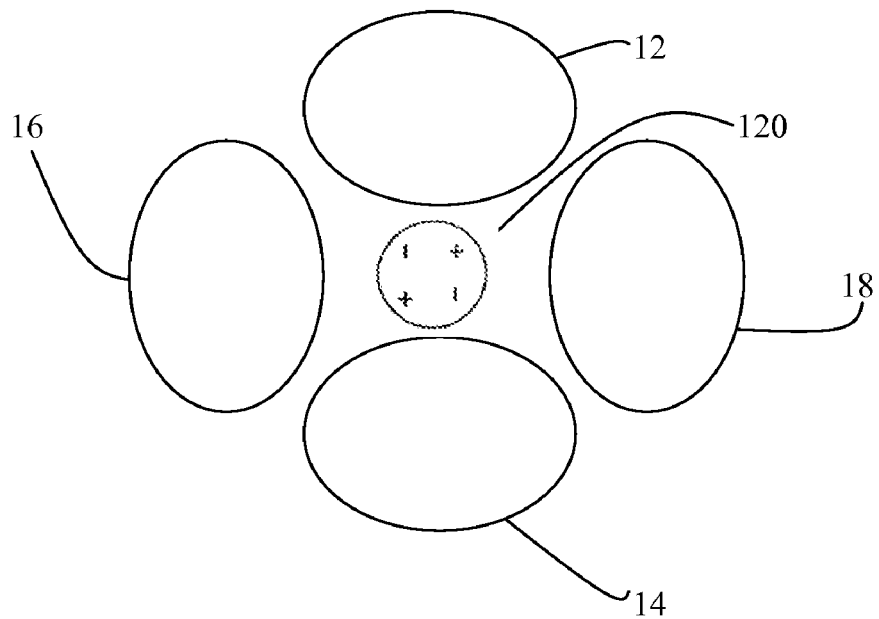
FIG. 5 illustrates another exemplary implementation showing an additional potential configuration of patient pads including a QMA located between the electrode pads.

In another implementation illustrated in FIG. 5, the apparatus is supplied with at least one QMA 120. This QMA can be placed in the middle of the pads 12, 14, 16, 18. In this implementation, the QMA 120 is placed over the site of pain on the individual and the electrode pads 12, 14, 16, 18 are placed "around" the pain. As a result, the settings needed on the TENS unit would need to be less to achieve the same benefit. The magnets therefore should be applied directly over the pain for maximum effectiveness of the magnet.

It is well known that the effectiveness of the treatment has been highly variable. It worked for some individuals and not for others. For an individual the placement of the electrodes 12, 14, 16, 18 of a TENS unit 10, either with or without the quadrapolar magnetic array (QMA), was a trial and error (empirical) process relying mainly on feedback from the individual being treated.

Magnet Component

In the currently disclosed apparatus, it was found that by using a magnetic field measuring device, such as a Gaussmeter, that the magnetic fields of the QMAs are surprisingly relatively independent of the tissue and bones present. Therefore, one can design a QMA that produces a particular magnetic field at any level above the QMA. The QMA arrangement provides the benefit of a steep field gradient as one moves across the magnets and this steep field gradient can be made any desirable level at any point above the QMA. The desired arrangements for the QMAs can be calculated using standard electromagnetic theory.

When the field of a single magnet anywhere in space is known, the fields of four magnets of the desired size and orientation can be combined at any point in space by the process of vector field addition. When the magnetization of a specific magnet is known or the magnetization of the magnets used in the QMA (which may be different) along with its dimensions, then one can combine the fields to calculate the total field of the QMAs. A typical example of the calculated field 108 for a QMA is shown in FIG. 8. The diagram gives the same values as the values obtained by constructing the QMA and using a Gaussmeter to measure the fields in space. The fields are given in milliTesla (mT) in FIG. 8. Magnetic fields are also described in the units of Gauss where 10 Gauss=1 mT.

In the plan view of a QMA 120 in FIG. 9 one creates the desired field and steep field gradient along the lines from the center of any magnet with a North pole facing the direction of the patient to the center of any magnet with a South pole facing an individual. In other words the steep field would not be in the center 122 of the QMA (point C as shown in FIG. 9) but at the four points between the edges of any two adjacent magnets 112, 116. In FIG. 9 one of these four points would be perpendicular to a line drawn from C 122 to B 124 from the two right most magnets. Four such points exists. The field of importance is the desired distance above the QMA that is "inside" the individual along these lines.

The total size of the QMA 120 was made to fit in about the same space as an electrode 12, 14, 16, 18 in a TENS unit 10. Thus, a two channel TENS unit 10 would have four such QMAs 120; one for each electrode 12, 14, 16, 18 as described in U.S. Pat. Nos. 6,205,356 or 6,741,889 and shown in FIG. 4.

In another implementation, the apparatus is supplied with at least one QMA 120. This QMA can be placed in the middle of the pads 12, 14, 16, 18. In this implementation, the QMA 120 is placed over the site of pain on the inivudal and the electrode pads 12, 14, 16, 18 are placed "around" the pain.

Using either the calculation technique or the measurement technique one skilled in the art is able to produce a QMA that provides the desired field and field gradient. In exemplary implementations, the QMA will be 1.5 mT in magnitude at the site of the pain with a steep gradient on either side.

Since it has been found that the magnetic field is surprisingly not affected by the tissue and bone, QMAs can be constructed and measured without reference to the physical body of the individual to be treated. This is not true of the electric field of the TENS unit itself which is strongly influenced by the body of the individual Thus, the following procedure and equipment to be described is of use any time one uses a TENS unit for pain relief either with or without magnetic augmentation.

The Electric Component:

Any wire or surface that conducts a current will emit an electric field when ever that current is increasing or decreasing. Thus, alternating current in wires emits a field continually. Direct currents such as those in the TENS units emit a field whenever they are pulsed. This field is transmitted in all direction and into the patient and results in the "action at a distance" when it interacts with the neuronal "firing". When neurons "fire" the conduction in the cell is related to a change in the sodium and potassium balance in "channels" that mediate the current flow in the cells.

The use of TENS unit has been almost totally empirical. In the past researchers have tried to measure surface currents of the TENS unit including skin impedance measurements. The information required to understand and influence what is occurring to the electric field is far below the surface at the site of the cells where the pain is transmitted.

Electric fields can be measured in space by using antennas connected to receiving circuits. In the case of simply measuring ambient electric fields from normal house wiring, for example, a simple dipole antenna can be used connected to an AC voltmeter. Usually the antenna is capacitively coupled to the voltmeter (by putting a capacitor of appropriate size for the filed one is measuring across the voltmeter input). Such devices can be calibrated with fields of known strength so that any AC voltmeter in the proper range can be used to measure such fields.

The Method:

Two dipoles antennas 70, 75 are used and the electrical fields are measured at two points in the vicinity of the TENS unit 10. When these readings from the first antenna 70 is compared to the other antenna 75, the value of the field between the two locations is deduced and an estimate of the electric field inside tissue is obtained.

These two antennas 70, 75 were fabricated such that they were placed within pads that are the same size as the TENS electrodes 12, 14, 16, 18. By placing the pads with the antennas 70, 75 in the vicinity of the TENS pads 12, 14, 16 18 one can measure the electric field and use that information to understand the settings of pulse amplitude, duration and pattern to insure delivering an effective amount of electric field to a desired location inside the individual being treated.

The Method comprises the following basic steps:
1) Use of a TENS unit 10 designed for pain relief.
2) Attaching two dipole antennas 70, 75 of size similar to or smaller than the electrodes used for the TENS current application in the vicinity of the TENS electrodes.
3) One antenna 70 is placed in an area or locations that will serve as a reference measurement either of the applied field or the background field.
4) The other antenna 75 is placed in a position to intercept all or a portion of the field going into the patient.
5) Using the ratio of these signals to modify the settings on the TENS units 10 to insure that an effective field is delivered to the site of interest.

The effective field was found to be different from individual to individual and was related to the depth of the affected cells, intervening tissue, etc. The system as described provides a rapid means to ensure that the field is known at the desired location and ensuring that the field can be manipulated by the TENS settings.

This method can be used with or without the magnetic augmentation. Since the magnetic field is static and is relatively unaffected by the tissue it does not change the conclusions from the electric field differences being measured. The magnet can be separately measured or calculated to deliver at least 1.5 mT at the desired location when they are used.

EXAMPLE A

TENS Measurement

The electric field from the AC of the TENS unit and DC magnetic field from the QMAs was measured separately. In a typical square pattern as previously shown for example in FIG. 6 one can only measure the magnetic field over the electrodes. There was no significant magnetic field off to the sides of the QMAs on each pad. The magnetic field that influences charged particles is not altered by the flesh to any measurable extent at the levels of precision in this test.

The AC electric field changed with the power level (increased) and the pulse width (slightly higher field for an 80 msec width than a 120 msec width).

The higher the pulse rate the higher the electric field. Thus the field was greater at 200 Hz than 80 Hz.

By changing the pulse rate one can increase the field at a given depth into the individual and thus the resistance to the field is proportional to the rate.

The waveshape of the pulses from the TENS unit changed the total field also. For any setting of the device, however, the pulse shape was the same.

Using 2.2 cm (22 mm) of "flesh" (30% fat bologna) the magnetic field was down to 1-2 mT. It other words it drops off the same as if the flesh was not there. The neurons in all directions have to pass through a zone of magnetism under the electrodes and provided a source of the effect.

Surprisingly the electric field was found to be larger at the center of the square when measured in the absence of flesh than it was over the pads. This indicated transmission through the air, plastic and meat by its magnetic field (not the DC magnetic field of the magnets).

When 22 mm of flesh was put over the pads the electric field was fairly uniform at the depth of 22 cm. This indicated that the strongest field carried along the surface of the flesh and a fairly uniform field penetrated the flesh.

At high rate (200 Hz) and pulse width (120 msec) the field decreased by about 70% when one used flesh that was 22 mm deep and had 30% fat content.

At lower rates (80 Hz) and pulse width (80 msec) it was found that the field was less at the surface and was about the same at 22 mm distance in the flesh.

There was found a difference between flesh with 30% fat content (beef bologna) and flesh with no fat content (turkey bologna). The lesser fat appeared to allow transmission of higher electric fields.

EXAMPLE B

TENS Measurement

In these sets of measurements beef bologna (30% fat) and turkey bologna (0% fat) were used in the experiments to represent flesh.

In the absence of "flesh" the electric field was larger at the center of the square than it was over the pads. Using the 0% fat turkey bologna and 30% fat beef bologna as "flesh" surrogates the magnetic field from the QMAs was the same with or without the flesh being present.

FIG. 10 shows the effect of measuring the electrical field at a distance of 22-24 mm in 0% fat and 30% fat "flesh" as represented by bologna. The data indicates that the fat affected the Electric field. The field was reduced by a significant amount from that measured in the 0% flesh.

FIG. 10 shows that the values at 22-24 mm depth in flesh do not increase as much with pulse width. Thus, the difference in the field increased with pulse width regardless of the fat content.

EXAMPLE 1

Test of Antenna System

Test that used the antenna circuit of the STENS unit to test the fields from an existing TENS unit.

The antenna circuitry of the STENS unit was used to measure the electrical fields of an existing marketed TENS unit. Measurements were made on a human which showed that the results obtained were similar to what was shown in the experiments with bologna of various fat content. When the electrodes were placed around the wrist (4 cm by 6 cm) one measured that the field would penetrate to the center at 2 cm from the location of the TENS unit. However, the field would not be sufficient when placed around most portions of the leg where the interior dimension was more than 2 cm from the surface. Further problems with the settings were found with the existing device.

EXAMPLE 2

Analgesic Effect

An individual was injected in the knee joint capsule. An eighteen gauge needle was used to penetrate the knee joint capsule. The needle skin penetration of the anterior knee joint was the pain stimulus. In addition intradermal capsaicin was used as a nociceptive stimuli. Using the TENS unit as described herein, an analgesic effect was produced, controlled and maintained throughout the trial. The pain from the skin penetration and capsaicin intradermal application was found to be easily controlled.

While the above description contains many particulars, these should not be considered limitations on the scope of the disclosure, but rather a demonstration of embodiments thereof. The apparatus and methods disclosed herein include any combinations of the different species or embodiments disclosed. Accordingly, it is not intended that the scope of the disclosure in any way be limited by the above description. The various elements of the claims and claims themselves may be combined in any combination, in accordance with the teachings of the present disclosure, which includes the claims.

The invention claimed is:

1. A method of producing analgesia in a mammal comprising:
    applying pulsed direct current to skin of said mammal;
    analyzing electric field produced by said pulsed direct current;
    modifying strength of said pulsed direct current based on measured said electric field;
    using at least two dipole antennas;
    placing one antenna for reference measurement;
    placing second antenna to measure all or partially the current field going to mammal; and
    using ratio of antenna signals to adjust setting wherein said dipole antennas are between about 1.5 inches to about 2.5 inches long and between about ¼ inch and about ¾ inch wide.

2. The method of claim 1 wherein the pulsed direct current has a duration between about 10 microseconds to about 1000 microseconds.

3. The method of claim 1 wherein the pulsed direct current has a duration between about 50 microseconds to about 500 microseconds.

4. The method of claim 1 wherein the pulsed direct current has a duration between about 100 microseconds to about 120 microseconds.

5. The method of claim 1 wherein the frequency of the pulsed direct current comprises between about 1 pulse per second to about 250 pulses per second.

6. The method of claim 1 wherein the frequency of the pulsed direct current comprises between about 100 pulse per second to about 225 pulses per second.

7. The method of claim 1 wherein the frequency of the pulsed direct current comprises between about 180 pulses per second to about 200 pulses per second.

8. The method of claim 1 wherein pulsed waveform is selected from the group consisting of monophasic, symmetrical biphasic, and asymmetrical biphasic.

9. The method of claim 1 wherein pulsed waveform is monophasic.

10. The method of claim 1 wherein the amplitude of the pulsed direct current is adjustable between about 1 mA to about 50 mA into a 1 kilo Ohm load.

11. The method of claim 1 wherein the amplitude of the pulsed direct current is between about 20 mA to about 40 mA.

12. The method of claim 1 wherein a pattern of the pulsed direct current is continuous or modulated wave shape.

13. The method of claim 12 wherein said pulsed pattern is a continuous wave shape.

14. A method of producing analgesia in a mammal comprising:
    applying pulsed direct current to skin of said mammal;
    analyzing electric field produced by said pulsed direct current;
    modifying strength of said pulsed direct current based on measured said electric field;
    using at least two dipole antennas;
    placing one antenna for reference measurement;
    placing second antenna to measure all or partially the current field going to mammal; and
    using ratio of antenna signals to adjust setting wherein the material of said dipole antenna is a conductor metal selected from the group consisting of copper, aluminum, and gold.

15. The method of claim 14 wherein said dipole antenna are between about 1.5 inches to about 2.5 inches long and between about ¼ inch and about ¾ wide.

16. The method of claim 14 wherein the pulsed direct current has a duration between about 10 microseconds to about 1000 microseconds.

17. The method of claim 14 wherein the pulsed direct current has a duration between about 50 microseconds to about 500 microseconds.

18. The method of claim 14 wherein the pulsed direct current has a duration between about 100 microseconds to about 120 microseconds.

19. The method of claim 14 wherein the frequency of the pulsed direct current comprises between about 1 pulse per second to about 250 pulses per second.

20. The method of claim 14 wherein the frequency of the pulsed direct current comprises between about 100 pulse per second to about 225 pulses per second.

21. The method of claim 14 wherein the frequency of the pulsed direct current comprises between about 180 pulses per second to about 200 pulses per second.

22. The method of claim 14 wherein pulsed waveform is selected from the group consisting of monophasic, symmetrical biphasic, and asymmetrical biphasic.

23. The method of claim 14 wherein pulsed waveform is monophasic.

24. The method of claim 14 wherein the amplitude of the pulsed direct current is adjustable between about 1 mA to about 50 mA into a 1 kilo Ohm load.

25. The method of claim 14 wherein the amplitude of the pulsed direct current is between about 20 mA to about 40 mA.

26. The method of claim 14 wherein a pattern of the pulsed direct current is continuous or modulated wave shape.

27. The method of claim 26 wherein said pulsed pattern is a continuous wave shape.

* * * * *